United States Patent [19]

Noding

[11] Patent Number: 4,689,123
[45] Date of Patent: Aug. 25, 1987

[54] NOVEL TETRAPHOSPHONIC ACID COMPOUNDS, INTERMEDIATES AND A PROCESS FOR THEIR PRODUCTION

[75] Inventor: Stephen A. Noding, Brusly, La.

[73] Assignee: The Dow Chemical Company, Midland, Mich.

[21] Appl. No.: 945,729

[22] Filed: Dec. 23, 1986

[51] Int. Cl.$^4$ ............................................. C25B 3/10
[52] U.S. Cl. .................................. 204/59 R; 556/405; 558/161
[58] Field of Search ...................... 204/59 R; 558/161; 556/405

[56] References Cited

U.S. PATENT DOCUMENTS

| | | | |
|---|---|---|---|
| 3,471,406 | 10/1969 | Budnick et al. | 558/161 |
| 3,639,239 | 1/1972 | Groenhof | 556/405 |
| 3,845,169 | 10/1974 | Maier | 558/161 |
| 4,001,352 | 1/1977 | Klewer et al. | 558/161 |
| 4,434,032 | 2/1984 | Baldwin et al. | 204/72 |
| 4,587,034 | 5/1986 | Sturtz et al. | 558/161 |

OTHER PUBLICATIONS

A Review of the Oxidative Electrochemical Coupling of Organic Anions, edited by Baizer, Organic Electrochemistry, Marcel Decker, Inc., New York, N.Y., p. 718 et seq., (1973).
Blackburn et al, Journal of Chemical Society, Chemical Communications, 1978, pp. 870 and 871.
Blackburn et al, J. C. S. Perkin I, 1980, pp. 1150–1153.
Morita et al, Journal of Chemical Society, Chemical Communications, pp. 874 and 875.
Morita et al, Tetrahedron Letters, No. 28, 1978, pp. 2523–2526.

*Primary Examiner*—Arthur P. Demers
*Attorney, Agent, or Firm*—D. R. Howard

[57] ABSTRACT

As novel compounds, ethane tetraphosphonate esters, including octaalkyl and trimethylsilyl esters, and ethylene tetraphosphonic acid, as well as new compositions including a mixture of the acid with tetramethyl methylene diphosphonic acid, and a process for the preparation thereof.

21 Claims, No Drawings

NOVEL TETRAPHOSPHONIC ACID COMPOUNDS, INTERMEDIATES AND A PROCESS FOR THEIR PRODUCTION

BACKGROUND OF THE INVENTION

This invention relates to novel tetraphosphonic acid compounds, intermediate tetraphosphonate ester compounds and processes for their production. Such compounds are believed to be unknown in the literature and likewise the processes for their production are unknown. More specifically, the present invention includes ethylene tetraphosphonic acid, intermediate octaalkyl ethanetetraphosphonate esters and certain other intermediates in the process for production of the tetraphosphonic acid composition. The process of the present invention includes an electrolytic coupling.

Although electrochemical coupling of radicals formed by anodic oxidation is known, previous processes have problems with selectivity, efficiency and expense. *A Review of the Oxidative Electrochemical Coupling of Organic Anions,* Edited by Baizer Organic Electrochemistry, Marcelle Decker, Inc., New York, N.Y., p. 718 et seq (1973), shows that acetonitrile is a preferred solvent when used with platinum electrodes. U.S. Pat. No. 4,434,032, to Baldwin et al, teaches an electrochemical coupling to produce a symmetrical alkanediol by first making a bis ether from a haloalkanol, then electrochemically coupling the bis ether by removal of the halo group, and finally de-etherifying to produce the desired alkanediol.

The dealkylation of phosphonic acid dialkyl esters by reaction with iodotrimethylsilane to produce the corresponding bistrimethylsilyl esters and the subsequent hydrolysis of these products to the parent phosphonic acids under mild conditions is described by Blackburn et al, Journal of the Chemical Society, Chemical Communications, 1978, pages 870–871, and J. C. S. Perkin I, 1980, pages 1150–1153. In a similar teaching, Morita et al, Journal of the Chemical Society, Chemical Communications, 1978, pages 874–875, teach the use of chlorotrimethylsilane and sodium iodide as a dealkylation agent for carboxylic acid esters to give the silyl derivatives, followed by simple conversion of the silyl derivatives to the corresponding carboxylic acids and phenols. Morita et al also teach a similar reaction of dialkyl phosphonates with chlorotrimethylsilane in the presence of sodium-iodide, followed by hydrolysis under mild conditions at Tetrahedron Letters, No. 28, 1978, pages 2523–2526.

SUMMARY OF THE INVENTION

The present invention provides a compound of the general formula,

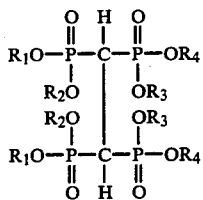

in which $R_1$, $R_2$, $R_3$, and $R_4$ are each independently selected from hydrogen, tri(lower alkyl)silyl, and alkyl groups having from 1 to about 20 carbon atoms. As another feature of the present invention, when the R groups are all methyl groups, the novel compound octamethyl 1,1,2,2-ethanetetraphosphonate is provided as a part of the present invention. The novel compound of the above general formula in which all of the R groups are hydrogen, which is ethylene tetraphosphonic acid, is also another feature of the present invention. The novel compound octatrimethylsilyl 1,1,2,2-ethanetetraphosphonate, in which all of the R groups in the above general formula are trilower alkyl silyl, is another feature of the present invention.

Another embodiment of the present invention is a direct electrochemical coupling without necessity for first making an intermediate derivative which features a process for the preparation of an octaalkyl ethanetetraphosphonate ester which comprises electrolytically coupling a diphosphonate compound of the formula,

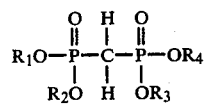

in which $R_1$, $R_2$, $R_3$, and $R_4$ are each independently selected from alkyl groups having from 1 to about 20 carbon atoms, dissolved in a polar solvent and in the presence of a guaternary ammonium halide electrolyte.

A further aspect of the invention includes a process for preparing an octa (tri(lower alkyl))silyl ethanetetraphosphonate ester in which the lower alkyl groups have from 1 to about 4 carbon atoms, which comprises converting an octaalkyl ethanetetraphosphonate ester in a polar solvent with iodotri(lower alkyl)silane.

A still further aspect of the present invention includes a process for the preparation of ethylene tetraphosphonic acid which comprises the steps of: (a) electrolytically coupling a diphosphonate compound of the formula,

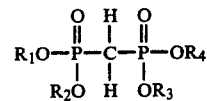

in which $R_1$, $R_2$, $R_3$, and $R_4$ are each independently selected from alkyl groups having from 1 to about 20 carbon atoms in a polar solvent and the presence of a quaternary ammonium halide to form an octaalkyl ethanetetraphosphonate ester; (b) converting the ester so formed to the trimethylsilyl ester by reacting said octaalkyl ethanetetraphosphonate ester with iodotri(lower alkyl)silane; and (c) hydrolysing the resultant tri(lower alkyl)silyl ester with water to form a composition containing ethylene tetraphosphonic acid. As a preferred embodiment of the present invention, the solvent employed in the process is acetonitrile and the electrodes are platinum. A further preferred embodiment employs a quaternary ammonium halide which is tetrabutylammonium iodide.

The process of this invention also provides as a new composition of matter a mixture comprising methylene diphosphonic acid and from about 10 to about 50 percent by weight, based on the weight of the mixture, of ethylene tetraphosphonic acid.

DESCRIPTION OF PREFERRED EMBODIMENTS

As indicated above, one aspect of the present invention is a new compound which is selected from a tetraphosphonate or tetraphosphonic acid. The compound has the general formula,

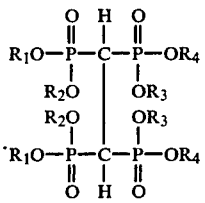

and each of the substituent groups, identified as $R_1$, $R_2$, $R_3$ and $R_4$, are each independently selected from hydrogen, tri(lower alkyl)silyl, and alkyl groups having from 1 to about 20 carbon atoms. The identity of the R groups in the final compound depends upon the starting material. Thus, if all of the R groups in the starting compound are methyl, then the starting tetraphosphonate will produce an octamethyl phosphonate. Subsequent conversion to the iodotri(lower alkyl)silane ester, preferably, iodotrimethyl silane ester, converts all of the original R groups to tri(lower alkyl)silyl groups and subsequent treatment can be employed to convert the tri(lower alkyl)silyl ester groups to phosphonic acid groups. Accordingly, if a mixed diphosphonate is employed, the corresponding mixed tetraphosphonate will result. However, subsequent conversion of the mixed tetraphosphonate to the tri(lower alkyl)silyl octa ester results in the corresponding tri(lower alkyl)silyl ester.

As indicated, in the product or intermediate compounds of the general formula I above, each of the substituent R groups can be independently selected from hydrogen, tri(lower alkyl)silyl and alkyl groups having from 1 to about 20 carbon atoms. Preferably, when the groups $R_1$, $R_2$, $R_3$ and $R_4$ are each independently selected from alkyl groups, the alkyl groups have from 1 to about 12 carbon atoms and more preferably from 1 to about 4 carbon atoms. Typical of the alkyl groups employed in preferred embodiments of the present compound are methyl, ethyl, propyl and butyl groups. Likewise, groups having up to 20 carbon atoms can be suitably employed, including pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl groups, together with the various positional isomers thereof, and provide useful substituents in the compound of the present invention having the general formula given above. The use of such alkyl groups results in the provision by the present invention of a phosphonate ester having attached thereto the ester radicals of the various alkyl groups identified above. Thus, a 1,1,2,2-ethanetetraphosphonate can have as the ester groups, eight methyl, ethyl, propyl or butyl groups. Most preferred is octamethyl 1,1,2,2-ethanetetraphosphonate.

Conversion of any of the foregoing octaalkyltetraphosphonate compounds with iodotrilower alkyl silane results in the formation of the corresponding octa(tri(lower alkyl))silyl ethanetetraphosphonate which is an intermediate compound of the present invention. In general, it is a matter of convenience as to which alkyl group is employed as a substituent in the ester radical because, when the alkyl ester is converted to the tri(lower alkyl)silyl ester, the octa(tri(lower alkyl))silyl ethanetetraphosphonate results in any case. However, some alkyl groups are displaced more readily and, therefore, make a more convenient form of the tetraphosphonate ester for conversion. Therefore, the tetraphosphonate ester having from 1–4 carbon atoms in each of the alkyl ester groups is a preferred intermediate compound for reaction with the iodotrilower alkyl silane. Preferably, the lower alkyl group employed in the trilower alkyl silane, as indicated above, is a lower alkyl group having from 1 to about 4 carbon atoms. Typically, such lower alkyl groups include methyl, ethyl, propyl and butyl groups. Most preferred of the lower alkyl groups is methyl, such that a most preferred iodo trilower alkyl silane is iodo trimethyl silane or trimethylsilyl iodide.

The octa(tri(lower alkyl))silyl ethanetetraphosphonate intermediate compound is desirable in order to produce the desired ethylenetetraphosphonic acid because direct hydrolysis of the alkyl esters has not been carried out heretofore so far as is presently known. However, it has been found that hydrolysis of the octa(trimethylsilyl)1,1,2,2-ethanetetraphosphonate results in the production of significant quantities of ethylene tetraphosphonic acid.

The ethylene tetraphosphonic acid and the foregoing intermediates identified hereinabove are produced in a process which includes the step of electrolytically coupling a diphosphonate compound of the formula,

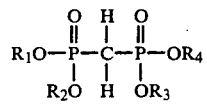

in which $R_1$, $R_2$, $R_3$, and $R_4$ are each independently selected from alkyl groups having from 1 to about 20 carbon atoms in which the electrochemical reaction takes place in a polar solvent and the presence of a quaternary ammonium halide to form an octaalkyl 1,1,2,2-ethanetetraphosphonate ester intermediate. The diphosphonate starting compound is known in the prior art and commercially available. However, it is believed that electrolytic coupling the diphosphonate starting compound to form the tetraphosphonate intermediate has not heretofore been known. The starting diphosphonate can have each of the substituent R groups, $R_1$, $R_2$, $R_3$ and $R_4$ independently selected or the same. The most simple and preferable process includes one in which each of the R groups are the same and, of course, in any process using a diphosphonate with different R groups, the resultant tetraphosphonate ester will have corresponding R groups as the ester substituents. A preferred starting diphosphonate is tetramethylenediphosphonate which is a pale yellow liquid.

The starting diphosphonate is preferably placed in an electrochemical cell, which is also preferably an undivided electrochemical cell, having an anode and a cathode. The anode and the cathode can be selected from conventional materials, such as stainless steel, nickel, iron, lead dioxide-TEFLON composite, graphite or platinum. Preferably, platinum is employed because it is inert in the reaction, highly stable under the conditions of electrolytic coupling, and electrically efficient. The starting diphosphonate can be placed in the electrochemical cell or first added to a polar solvent.

The solvent facilitates carrying the current between the electrodes and maintains the product and starting material in solution. Preferably, the solvent is one which maintains the reactant and products in solution and has a relatively high dielectric constant, usually greater than about 30. It should remain fluid and be sufficiently volatile to be easily removed from any products by evaporation. Typical nitrile solvents useful in this invention are acetonitrile, propionitrile, butyronitrile and benzonitrile. Alcohol solvents, such as, methanol, ethanol, isopropanol and butanol, may also be employed provided that the alcohol used has a hydrocarbyl group which is the same as the alkyl group of the starting diphosphonate. This prevents the formation of mixed ester tetraphosphonates where such are not desired. Certain heterocyclic solvents may also be employed in the process of this invention, e.g., furans, such as, tetrahydrofuran; thiophene; pyrrole; and the like being typical examples. More preferred are the nitrile and furan solvents; of which the more particularly preferred are acetonitrile or tetrahydrofuran. However, acetonitrile is most preferred because it is more efficient than the alcohol solvents and results in higher current-carrying capacity for the electrochemical cell.

The electrochemical coupling of the present process is carried out at a voltage of from about 5 to about 20 volts and a current of from about 25 to about 75 milliamps/in$^2$ (3.8–11.5 milliamps/cm$^2$). The reaction is carried out for a period sufficient to convert a substantial amount of the diphosphonate to the coupled tetraphosphonate ester. Typically, the reaction can be carried out for a period of from about 2 to about 4 hours. However, the time of reaction depends to a great extent on the voltage and the current involved, as well as, the reaction temperature, and the concentration in the reaction mixture of the starting diphosphonate. Therefore, reaction time is not a truly independent variable.

The reaction is carried out at a temperature within the range of about 25° to about 60° C. depending on the use of stirring or cooling in the electrochemical cell. Typically, the reaction begins at a reaction mixture temperature of about ambient temperatures and generally the temperature rises to about 50° or 60° C.

Also added to the reaction mixture is a source of iodide ion as an electrolyte which is converted at the anode to iodine thereby providing electrons for the coupling reaction, i.e., the diphosphonate to produce the tetraphosphonate, at the cathode. Without being limited to any theory or method, it is believed that the iodine formed at the anode complexes with the central carbon atom of the diphosphonate anion formed in the electrolyte at the cathode and this iodomethylene diphosphonate complex subsequently contacts another methylene diphosphonate anion, reacts therewith and forms the coupled product. In order to minimize by-product formation, the concentration of starting diphosphonate in the reaction mixture should be low. The more dilute the solution, the better the yields and conversions of the diphosphonate to the tetraphosphonate will be. Preferably, the concentration of the diphosphonate compound in the preferred acetonitrile solvent is from about 0.5 molar to about 0.05 molar, and, more preferably, from about 0.3 molar to about 0.1 molar solution. Another advantage of carrying out the reaction in a dilute solution is the lower by-product formation. Specifically, the formation of ylide salts from the diphosphonate ester has been noted at higher concentrations.

The quaternary ammonium halide added to the reaction mixture is preferably a quaternary ammonium iodide. Although metal halides, particularly potassium iodide, can be used, it has been found that the metal ions interfere with subsequent process steps, particularly conversion to the acids and silyl esters. A quaternary ammonium iodide is more preferred, such as a tetraalkylammonium iodide having from about 2 to about 4 carbon atoms in the alkyl groups. Most preferable is tetrabutylammonium iodide. Mixed quaternary ammonium iodides, such as methyltributyl, butyltrimethyl, and other well known quaternary ammonium iodides, can also be employed in the process of the present invention. The quaternary ammonium halide is present at a concentration of from about 0.5 to about 0.15 percent by weight, based on the starting diphosphonate compound.

When acetonitrile is employed as a solvent, it is not necessary to separate the intermediate product from the reaction mixture. Silylation can take place directly in the reaction mixture simply by cooling the reaction mixture to a temperature of about 0° to about 10° C. with stirring and adding liquid tri(lower alkyl)silyl iodide. However, when an alcohol solvent is employed, the alcohol is removed by vaccum distillation before adding the tri(lower alkyl)silyl iodide. At least stoichiometric amounts are required and preferably at least 8 moles of the tri(lower alkyl)silyl iodide are used for each mole of starting diphosphonate. The reaction mixture is allowed to warm to room temperature or is heated up to about 45° C. with stirring and then is allowed to stand for several hours. Thereafter, the solvent can be evaporated with the aid of vacuum at 20° to 30° C. and the tri(lower alkyl)silyl tetraphosphonate ester remains in the reaction vessel together with some of the monomeric starting diphosphonate and other by-products including the iodide and iodine from the electrolytic coupling process.

The hydrolysis step is then fairly straightforward because it is only necessary to add sufficient water to hydrolyze the tri(lower alkyl)silyl groups and stir the reaction mixture at room temperature for several hours until a solid precipitate forms. Workup of the reaction mixture includes filtering the solid precipitate and subsequent removal of any hydrated water under vacuum to produce the tetraphosphonic acid.

Analysis of product mixtures from the hydrolysis indicates at most a 50 weight percent mixture containing the tetraphosphonic acid. It is unknown whether the intermediate tetraphosphonate ester did not form or by-products were produced or whether the coupled ester carbon-carbon bond is too weak to withstand the entry of the large trimethylsilyl groups and causing cleavage. However, by whatever mechanism or method the reaction occurs, it is clear that the ethylene tetraphosphonic acid is produced. Thus, another aspect of the present invention is a new composition of matter which is a mixture comprising methylene diphosphonic acid and from about 10 to about 50 percent by weight, and more preferably about a 50 percent by weight, based on the weight of the total mixture, of ethylene tetraphosphonic acid. The process of the present invention can be more fully illustrated by reference to the following examples.

EXAMPLES

In general, the procedure for the electrochemical coupling step was carried out by employing a 500-milliliter undivided polytetrafluoroethylene electrochemical cell having two-one square inch (6.45 cm²) platinum electrodes connected to a power source. To the cell was added about 300 milliliters of solvent and sufficient starting methylene diphosphonate to provide a 0.1 molar solution. Cell voltage applied ranged from about 3 to about 6.0 volts and a current of from about 100 to about 250 milliamps/in² (15.5–38.8 milliamps/cm²) was impressed. Cell temperatures ranged from ambient at the beginning of the reaction to about 50° C. After operation for a period of about 4 hours, the cell was cooled and 8 moles of iodotrimethyl silane per mole of starting diphosphonate were added. The reaction mixture was then stirred for about 2–4 hours at temperatures up to about 40° C. Then, the solvent was evaporated under vacuum at about 20° to 30° C. and sufficient water added to hydrolyze the resultant reaction mixture to the corresponding phosphonic acid. The precipitate formed on hydrolysis was worked up by filtration and evaporative drying under vacuum. Analysis by proton, C-13, and P-31 NMR confirms the structures. Melting points were taken and yields calculated. Samples of the intermediate were not taken before silylation and hydrolysis or analyzed because of the sensitivity of such intermediates. However, their presence is inferred because the octamethyl 1,1,2,2-ethanetetraphosphonate must be the source of the final product.

The following Table contains the results of several experiments in accord with the present invention and several comparative experiments.

TABLE

Preparation of Octaalkylethylene Tetraphosphonate, Octatrimethylsilylethylene Tetraphosphonate and Ethylene Tetraphosphonic Acid

| Ex. No. | Starting Material | Electrolyte | Solvent | Current | Cell Voltage | Trimethyl Iodosilane | Product | Comments |
|---|---|---|---|---|---|---|---|---|
| 1. | tetramethyl methylene diphosphonate | tetrabutyl ammonium iodide | acetonitrile | 200 | ~3.5 | 4:1 | 50% methylene diphosphonic acid 50% ethylene tetraphosphonic acid | Electrolytic coupling at 60° C. |
| 2. | tetramethyl methylene diphosphonate | tetrabutyl ammonium iodide | acetonitrile | 200 | ~5 | 4:1 | 50% methylene diphosphonic acid 50% ethylene tetraphosphonic acid | Electrolytic coupling at 35° C. |
| Comparative Examples | | | | | | | | |
| A. | tetramethyl methylene diphosphonate | potassium iodide | methanol | 100 | ~3.5 | — | yellow solid potassium complex | No coupling product |
| B. | tetramethyl methylene diphosphonate | potassium iodide | acetonitrile | 250 | ~5.5 | — | 25% yield of yellow solid potassium complex below | No coupling product |
| C. | tetraethyl methylene diphosphonate | sodium iodide | acetonitrile | 200 | ~5.7 | — | 70% yield of yellow solid sodium complex | See comment in Comparative Experiment B Above |
| D. | tetramethyl methylene diphosphonate | potassium iodide | acetonitrile | 200 | ~5 | 4:1 | diphosphonic acid | Water added after acetonitrile and by-products removed by vacuum. |
| E. | tetraethyl methylene diphosphonate | sodium iodide | acetonitrile | 200 | ~5 | 4:1 | diphosphonic acid | Water added after acetonitrile and by-products removed by vacuum. |

$$\begin{array}{c} \phantom{xx}K^+ \\ \phantom{xx}/\phantom{xx}\backslash \\ -\overset{|}{O}\phantom{xx}\overset{\|}{O} \\ MeO-P=C-P-OMe \\ |\phantom{xx}H\phantom{xx}| \\ MeO\phantom{xxx}OMe \end{array}$$

From the foregoing Table, it is apparent that the Examples of the present invention provide the desired intermediates and products as described. However, use of metal halide electrolytes causes the formation of ylide salts and inhibits the preparation of the tetraphosphonates or tetraphosphonic acids corresponding to the present invention.

The ethylene tetraphosphonic acids are employed as chelating agents, having the ability to bind metals within the molecular structure by hydrogen and electrostatic bonding forces. Such properties find ready use in metal and metal ion removal in water treating, medical and similar applications. The tetraphosphonates likewise display chelation activity, but to a lesser degree than the tetraphosphonic acids. The trimethylsilyl ethylene tetraphosphonates appear to be critical intermediates to the preparation of the tetraphosphonic acids, so far as is presently known.

Having described the present invention, one skilled in the art can readily envision changes and modifications to the present invention which are nevertheless within

I claim:
1. A compound of the general formula:

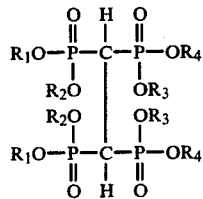

wherein $R_1$, $R_2$, $R_3$, and $R_4$ are each independently selected from hydrogen, trimethylsilyl, and alkyl groups having from 1 to about 20 carbon atoms.

2. The compound of claim 1 wherein $R_1$, $R_2$, $R_3$, and $R_4$ are each independently selected from alkyl groups having from 1 to about 12 carbon atoms.

3. The compound of claim 1 wherein $R_1$, $R_2$, $R_3$ and $R_4$ are each independently selected from alkyl groups having from 1 to about 4 carbon atoms.

4. The compound of claim 1 in which $R_1$, $R_2$, $R_3$, and $R_4$ are each the same and are alkyl groups selected from methyl, ethyl, propyl, and butyl groups.

5. The compound of claim 1 which is octamethyl 1,1,2,2-ethanetetraphosphonate.

6. The compound of claim 1 which is ethylene tetraphosphonic acid.

7. The compound of claim 1 which is octatrimethylsilyl 1,1,2,2-ethanetetraphosphonate.

8. A process for preparation of ethylene tetraphosphonic acid which comprises the steps of:
(a) electrolytically coupling a diphosphonate compound of the formula,

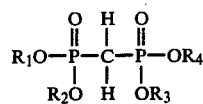

in which $R_1$, $R_2$, $R_3$, and $R_4$ are each independently selected from alkyl groups having from 1 to about 20 carbon atoms, dissolved in a polar solvent and in the presence of a quaternary ammonium halide to form an octaalkyl ethanetetraphosphonate ester;

(b) converting the ester so formed to its corresponding trimethylsilyl ester by reacting said octaalkyl 1,1,2,2-ethanetetraphosphonate ester with iodotrimethylsilane; and (c) hydrolysing the resultant trimethylsilyl ester with water to form a composition containing ethylene tetraphosphonic acid.

9. The process of claim 8 in which said solvent is acetonitrile.

10. The process of claim 8 in which the electrolytic coupling of said step (a) is carried out in an undivided electrochemical cell having an anode and a cathode at a voltage of about 5 to about 20 volts and a current of from about 25 to about 75 milliamps/in$^2$ (3.8–11.5 milliamps/cm$^2$).

11. The process of claim 10 in which said anode and said cathode are platinum.

12. The process of claim 8 in which the concentration of said diphosphonate compound in said solvent is from about 0.5 molar to about 0.05 molar.

13. The process of claim 8 in which said quaternary ammonium halide is a quaternary ammonium iodide.

14. The process of claim 13 in which said quaternary ammonium iodide is a tetraalkyl ammonium iodide having from 2 to about 4 carbon atoms in each alkyl group.

15. The process of claim 14 in which said tetraalkyl ammonium iodide is tetrabutylammonium iodide.

16. The process of claim 15 in which said tetrabutylammonium iodide is present at a concentration of from about 0.5 to about 0.15 percent by weight based on said diphosphonate compound.

17. The process of claim 8 in which the electrolytic coupling reaction of step (a) is carried out at a temperature from about 25° to about 60° C.

18. The process of claim 8 in which said step (b) is carried out with stirring at a temperature of from about 30° to about 45° C.

19. The process of claim 18 wherein said hydrolyzing of said step (c) is carried out at a temperature of about 20° to about 30° C.

20. The process of claim 8 wherein said composition is a mixture of methylene diphosphonic acid and from about 10 to about 50 percent by weight based on the weight of the mixture of ethylene tetraphosphonic acid.

21. As a new composition of matter, a mixture comprising methylene diphosphonic acid and from about 10 to about 50 percent by weight based on the weight of the mixture of ethylene tetraphosphonic acid.

* * * * *